United States Patent
Aso et al.

(10) Patent No.: US 8,985,144 B2
(45) Date of Patent: Mar. 24, 2015

(54) LOW-PRESSURE GRADIENT DEVICE

(75) Inventors: Yoshiaki Aso, Kyoto (JP); Fujio Inoue, Kyoto (JP)

(73) Assignee: Shimadzu Corporation, Kyoto (JP)

(*) Notice: Subject to any disclaimer, the term of this patent is extended or adjusted under 35 U.S.C. 154(b) by 508 days.

(21) Appl. No.: 13/330,839

(22) Filed: Dec. 20, 2011

(65) Prior Publication Data

US 2013/0008535 A1 Jan. 10, 2013

(30) Foreign Application Priority Data

Jul. 5, 2011 (JP) ................................ 2011-149328

(51) Int. Cl.
  *G01N 1/38* (2006.01)
  *B01F 5/06* (2006.01)
  *G01N 30/34* (2006.01)

(52) U.S. Cl.
  CPC .................................... *G01N 30/34* (2013.01)
  USPC ............ 137/606; 73/61.56; 73/61.57; 422/70

(58) Field of Classification Search
  USPC ................. 137/606; 73/61.56, 61.57; 422/70; 210/198.2
  See application file for complete search history.

(56) References Cited

U.S. PATENT DOCUMENTS

| 4,475,821 | A | * | 10/1984 | Koch et al. | ................. | 366/160.1 |
| 5,950,675 | A | * | 9/1999 | Minami et al. | ................. | 137/606 |
| 8,182,236 | B2 | * | 5/2012 | Shaimi | ............................ | 417/53 |
| 2006/0045810 | A1 | * | 3/2006 | Choikhet et al. | ............... | 422/100 |
| 2011/0100362 | A1 | * | 5/2011 | Baecke et al. | ............ | 128/203.12 |

FOREIGN PATENT DOCUMENTS

JP     5-312795 A     11/1993

* cited by examiner

*Primary Examiner* — Atif Chaudry
(74) *Attorney, Agent, or Firm* — Westerman, Hattori, Daniels & Adrian, LLP (57) ABSTRACT

A plurality of suctioning flow paths for suctioning mobile phases meet each other at a meeting portion. The meeting portion is connected to an inlet flow path communicating with an inlet of a reciprocating pump. The suctioning flow paths are respectively provided with solenoid valves for opening and closing the respective flow paths. The suctioning flow paths are respectively provided with orifices between the solenoid valves and the meeting portion. The orifices are sections of the respective suctioning flow paths having smaller diameters.

10 Claims, 6 Drawing Sheets

Organic Solvent Mobile Phase →     ← Water Mobile Phase

Back-flow Section

LOW-PRESSURE GRADIENT DEVICE

BACKGROUND OF THE INVENTION

1. Field of the Invention

The present invention relates to a gradient device for changing, over time, a composition of a mobile phase sent through an analytical flow path of a liquid chromatograph, and particularly to a low-pressure gradient device.

2. Description of the Related Art

As a liquid chromatograph, there is one including a low-pressure gradient device for supplying a mobile phase to an analytical flow path while changing its composition over time (refer to Japanese Patent Application Laid-Open No. 5-312795, for example). In such a low-pressure gradient device, generally, a plurality of kinds of liquids are prepared and times when the liquids are suctioned into a reciprocating pump, such as a plunger pump, are controlled to adjust a mixing ratio of the liquids to thereby change the composition of the mobile phase.

Figure 6:
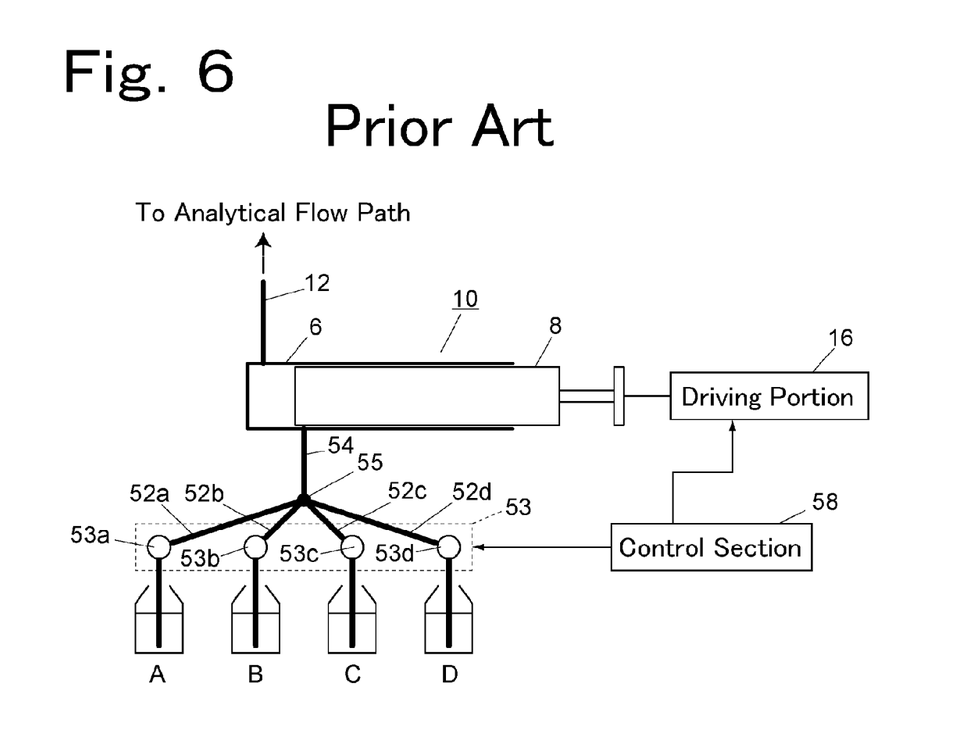
FIG. 6 is a flow path block diagram schematically showing an example of a prior-art gradient device.

FIG. 6 shows an example of a prior-art low-pressure gradient device.

There is a plunger pump 10 for suctioning and discharging liquids by sliding of a plunger 8 in a pump head 6, an inlet flow path 54 is connected to a liquid inlet of the plunger pump 10, and an outlet flow path 12 is connected to a liquid outlet. The plunger 8 is driven to reciprocate on a straight line by a driving portion 16 including a motor and a cam mechanism, and operation of the driving portion 16 is controlled by a control section 58.

As the mobile phases to be sent by the plunger pump 10, four kinds of mobile phases A to D are prepared. Suctioning flow paths 52a to 52d having one of their ends for respectively suctioning the mobile phases A to D have the other ends meeting each other at a meeting portion 55 and connected to the inlet flow path 54. A switching mechanism 53 formed to open only one of the suctioning flow paths 52a to 52d is provided. The switching mechanism 53 includes opening/closing valves 53a to 53d provided on the respective suctioning flow paths 52a to 52d and allows only one of the mobile phases to be suctioned into the plunger pump 10. Operation of the switching mechanism 53 is controlled by a control section 58. Although it is not shown in the drawing, the inlet flow path 54 and the outlet flow path 12 are respectively provided with check valves, the inlet flow path 54 is open and the outlet flow path 12 is closed during a suctioning operation of the plunger pump 10, and the outlet flow path 12 is open and the inlet flow path 54 is closed during a discharge operation of the plunger pump 10.

In the gradient device, two of the four kinds of mobile phases A to D, for example, are successively suctioned into the plunger pump 10 and mixed by switching the flow path at a predetermined time, and the mixed liquid is sent into an analytical flow path of the liquid chromatograph. By changing times when the mobile phases to be suctioned into the plunger pump 10 are switched over time, the composition of the mobile phase to be sent into the analytical flow path is changed.

Although the mobile phases to be suctioned into the plunger pump 10 come in contact with each other at the meeting portion 55 in the above-described gradient device, only the suctioning flow path of the mobile phase to be suctioned into the plunger pump 10 is open and the suctioning flow paths of the other mobile phases are closed, and therefore, another mobile phase does not flow back into the closed suctioning flow paths. However, it was found that the mobile phase having a higher density flows into (flows back into) the flow path for the mobile phase having a lower density, if there is a difference in density between the mobile phases in contact with each other. If the mobile phase flows back, the mobile phase that should be suctioned into the plunger pump 10 flows into the flow path for the other mobile phase, and therefore, a predetermined quantity to be suctioned cannot be achieved, which affects the composition of the mobile phase sent from the plunger pump 10, and reproducibility of an analysis result of the liquid chromatograph cannot be obtained.

SUMMARY OF THE INVENTION

It is therefore an object of the present invention to suppress back-flow of a mobile phase caused by a difference in density between mobile phases.

The present invention is a gradient device including: a reciprocating pump for sending a liquid by suctioning and discharging the liquid; a first suctioning flow path for introducing a first mobile phase into the reciprocating pump; a second suctioning flow path for introducing a second mobile phase into the reciprocating pump; a meeting portion where the first suctioning flow path and the second suctioning flow path meet each other; an inlet flow path connecting the meeting portion and the reciprocating pump to introduce the liquid from the first suctioning flow path or the second suctioning flow path into the reciprocating pump; solenoid valves respectively provided on the first suctioning flow path and the second suctioning flow path to carry out opening and closing of the respective flow paths at different times; and orifices provided as flow path sections having smaller diameters between the solenoid valves and the meeting portion on the respective suctioning flow paths.

Here, the "orifice" refers to a portion of the flow path and having a smaller inner diameter than the other flow path portion. Instead of the flow path portion having the smaller inner diameter, the orifice may be a plate interrupting the flow path and having a small hole. If such an orifice is provided on each of the suctioning flow paths, it is possible to suppress back-flow of the mobile phase into each of the suctioning flow paths farther than the orifice from the other suctioning flow path.

For a low-pressure gradient analysis of a liquid chromatograph, a water solvent and an organic solvent such as acetonitrile are used often. A representative water solvent is a buffer solution such as a phosphate buffer solution. If the buffer solution is mixed with the organic solvent, salt dissolved in the buffer solution is deposited. If the buffer solution and the organic solvent are used in the gradient device, the buffer solution flows back into a flow path for the organic solvent and salt is deposited in the flow path for the organic solvent. If the salt is deposited on or near a solenoid valve for opening and closing the flow path for the organic solvent, the deposited salt may enter between a valve element and a valve seat of the solenoid valve to impair liquid-tightness between the valve element and the valve seat when the valve is closed and the solenoid valve may not be closed completely in some cases.

In the gradient device in the present invention, if, for example, the first mobile phase is the organic solvent and the second mobile phase is the water solvent the water solvent flowing into the first suctioning flow path is prevented from reaching the solenoid valve because the orifice is provided between the solenoid valve and the meeting portion in the first suctioning flow path. Therefore, it is possible to prevent deposition of the salt on the solenoid valve.

An inner diameter of each of the orifices is preferably half an inner diameter of the suctioning flow path provided with the orifice or smaller. In this way, it is possible to increase an effect of preventing back-flow of the solvent in the suctioning flow path provided with the orifice.

According to the gradient device in the present invention, the orifice having the smaller inner diameter is provided between the solenoid valve and the meeting portion in each of the suctioning flow paths including at least the first suctioning flow path, and therefore, the orifice can suppress the back-flow of the second mobile phase having a higher density than the first mobile phase from the second flow path into the first suctioning flow path.

In a preferred embodiment of the present invention, the low-pressure gradient device may have at least one further suctioning flow path for introducing another mobile phase into the reciprocating pump. The further suctioning flow path is also connected to the meeting portion, and the further suctioning flow path is also provided with respective solenoid valve and orifice. That is, in case that a third mobile phase is also used the third suctioning flow path is further connected to the meeting portion, and in case that a fourth mobile phase is also used the fourth suctioning flow path is further connected to the meeting portion as shown in the example.

BRIEF DESCRIPTION OF THE DRAWINGS

FIGS. 2A and 2B are diagrams showing a structure of a switching mechanism portion in the embodiment, wherein FIG. 2A is a top view and FIG. 2B is a sectional view at a position X-X in FIG. 2A;

FIGS. 4A and 4B are diagrams showing results of simulations of states in respective flow paths in suctioning an organic solvent mobile phase and a water mobile phase into a reciprocating pump, wherein FIG. 4A shows a case in which neither of the flow paths is provided with the orifice and FIG. 4B shows a case in which the flow path for the organic solvent mobile phase is provided with the orifice;

FIGS. 5A and 5B are conceptual diagrams of space in a meeting block where suctioning flow paths meet each other, wherein FIG. 5A is the conceptual diagram of the meeting block seen from the front and FIG. 5B is the conceptual diagram of the meeting block seen from above.

DETAILED DESCRIPTION OF THE INVENTION

An embodiment of a low-pressure gradient device of a liquid chromatograph will be described with reference to FIG. 1.

The gradient device includes a plunger pump 10 as an example of a reciprocating pump for suctioning and discharging a liquid to thereby send the liquid. The plunger pump 10 includes a pump head 6 and a plunger 8 and an inlet flow path 4 and an outlet flow path 12 are connected to the pump head 6. The plunger 8 is driven to reciprocate on a straight line by a driving portion 16 having a motor and a cam mechanism so as to slide in the pump head 6.

When the plunger 8 slides in the pump head 6, the liquid is suctioned into the pump head 6 from the inlet flow path 4 and the suctioned liquid is discharged from the outlet flow path 12. Although it is not shown in the drawing, check valves for respectively preventing back-flows are provided on the inlet flow path 4 and the outlet flow path 12, the inlet flow path 4 is opened while the outlet flow path 12 is closed during a suctioning operation, and the outlet flow path 4 is opened and the inlet flow path 4 is closed during a discharge operation.

In this gradient device, the plunger pump 10 can send four kinds of mobile phases A to D separately or in mixture. The suctioning flow paths 2a to 2d for respectively suctioning the mobile phases A to D meet each other at a meeting portion 5 and are connected to one end of the inlet flow path 4.

In case only two kinds of mobile phases are used the gradient device may be provided with only two suctioning flow paths, and in case only three kinds of mobile phases are used the gradient device may be provided with only three suctioning flow paths. When more than four kinds of mobile phases are used, the gradient device may be provided with the same number of the suctioning flow paths as the mobile phases.

A switching mechanism 3 for controlling opening and closing of the respective suctioning flow paths 2a to 2d is provided. The switching mechanism 3 includes solenoid valves 3a to 3d provided on the respective suctioning flow paths 2a to 2d and can open and close the respective solenoid valves 3a to 3d at different times.

Orifices 14a to 14d are provided between the respective solenoid valves 3a to 3d of the suctioning flow paths 2a to 2d and the meeting portion 5. The orifices 14a to 14d are sections in the respective suctioning flow paths 2a to 2d and having smaller inner diameters. When a high-density mobile phase is suctioned into the plunger pump 10 from any one of the suctioning flow paths, the high-density mobile phase may flow into the suctioning flow path for a low-density mobile phase in some cases. However, the back-flow is suppressed by the orifice having the smaller inner diameter and prevented from reaching the solenoid valve provided to the flow path.

By setting the inner diameters of the orifices 14a to 14d to half inner diameters of the suctioning flow paths 2a to 2d or smaller, it is possible to enhance the effect of holding back the mobile phase flowing back from another suctioning flow path. If the inner diameters of the suctioning flow paths 2a to 2d are about 1 to 2 mm, for example, the inner diameters of the orifices 14a to 14d are preferably about 0.3 to 0.6 mm, for example.

An example of a specific structure of the switching mechanism 3 in the gradient device in the embodiment will be described with reference to FIGS. 2A and 2B.

The switching mechanism 3 in this example includes a connecting block 20 having a plurality of ports and flow paths for connecting the ports. The connecting block 20 is a rectangular parallelepiped and the solenoid valves 3a to 3d are respectively attached to four peripheral faces of the connecting block 20. Packing 29 for increasing hermeticity of each of flow path joint sections is inserted into a mounting portion of each of the solenoid valves 3a to 3d in the peripheral face of the connecting block 20.

Each of the solenoid valves 3a to 3d has an inlet flow path and an outlet flow path and switches between connection and disconnection of the inlet flow path and the outlet flow path to and from each other by driving, for example, a diaphragm valve. Although the solenoid valve 3a has the inlet flow path 27a and the outlet flow path 28a, the solenoid valve 3b has the inlet flow path 27b and the outlet flow path 28b, the solenoid valve 3c has the inlet flow path 27c and the outlet flow path 28c, and the solenoid valve 3d has the inlet flow path 27d and the outlet flow path 28d, respectively, only the inlet flow paths 27a and 27c and the outlet flow paths 28a and 28c are shown in FIG. 2B.

Figure 3:
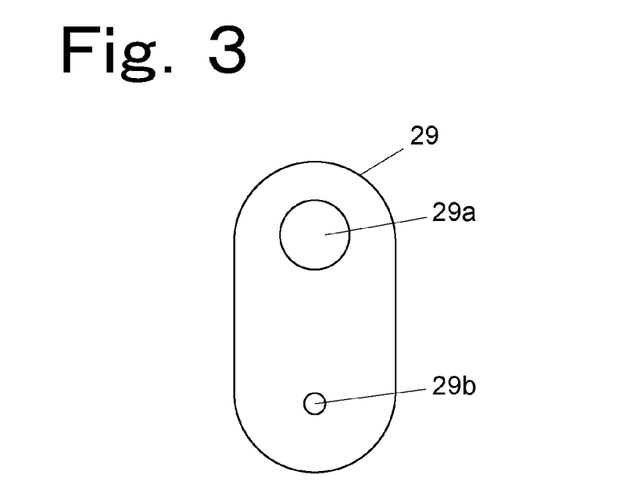
FIG. 3 is a diagram showing an example of a structure of an orifice in the embodiment.

As shown in FIG. 3, the packing 29 has a flow path opening 29a at a position corresponding to each of the inlet flow paths 27a to 27d of the respective solenoid valves 3a to 3d and a flow path hole 29b at a position corresponding to each of the outlet flow paths 28a to 28d.

Inlet ports 22a to 22d and an outlet port 24 are formed in an upper face of the connecting block 20. The inlet ports 22a to 22d are ports to which pipes forming the suctioning flow paths 2a to 2d (FIG. 1) for suctioning the mobile phases A to D are connected. The outlet port 24 is a port to which one end of a pipe forming the inlet flow path 4 (FIG. 1) connected to a suctioning port of the plunger pump 10 is connected.

The inlet ports 22a to 22d are formed to correspond to the solenoid valves 3a to 3d, respectively. In other words, the inlet port 22a is provided on a side of the solenoid valve 3a, the inlet port 22b is provided on a side of the solenoid valve 3b, the inlet port 22c is provided on a side of the solenoid valve 3c, and the inlet port 22d is provided on a side of the solenoid valve 3d, respectively. The outlet port 24 is formed at a position near a center of the upper face of the connecting block 20 while surrounded with the inlet ports 22a to 22d.

In the connecting block 20, a flow path 26a for connecting the inlet port 22a and the inlet flow path 27a of the solenoid valve 3a, a flow path 26b for connecting the inlet port 22b and the inlet flow path 27b of the solenoid valve 3b, a flow path 26c for connecting the inlet port 22c and the inlet flow path 27c of the solenoid valve 3c, and a flow path 26d for connecting the inlet port 22d and the inlet flow path 27d of the solenoid valve 3d are provided. Out of the flow paths 26a to 26d, only the flow paths 26a and 26c are shown in FIG. 2B. The flow paths 26a to 26d are respectively connected to the inlet flow paths 27a to 27d through the flow path openings 29a in the pieces of packing 29.

Furthermore, in the connecting block 20, flow paths 30a to 30d having one of their ends connected to the outlet flow paths 28a to 28d of the solenoid valves 3a to 3d through the flow path holes 29b in the pieces of packing 29 are provided. The other ends of the flow paths 30a to 30d meet each other at a meeting portion 31 and are connected to a flow path 32 connected to the outlet port 24.

Inner diameters of the flow paths 26a to 26d and 30a to 30d provided in the connecting block 20 are about 1 to 2 mm. The flow path opening 29a in each of the pieces of packing 29 has an inner diameter of about 1 to 2 mm which is about the same as the inner diameters of the flow paths 26a to 26d and 30a to 30d. On the other hand, the flow path hole 29b has an inner diameter of about 0.3 to 0.6 mm to form each of the orifices 14a to 14d in FIG. 1. In this way, in suctioning the mobile phase into the reciprocating pump connected to the outlet port 24, even if the mobile phase to be suctioned into the outlet port 24 through any one of the flow paths 30a to 30d flows back into another flow path due to a difference in density from the mobile phase filling each flow path, the back-flow is suppressed in the packing 29 and prevented from reaching each of the solenoid valves 3a to 3d.

Figure 4A:
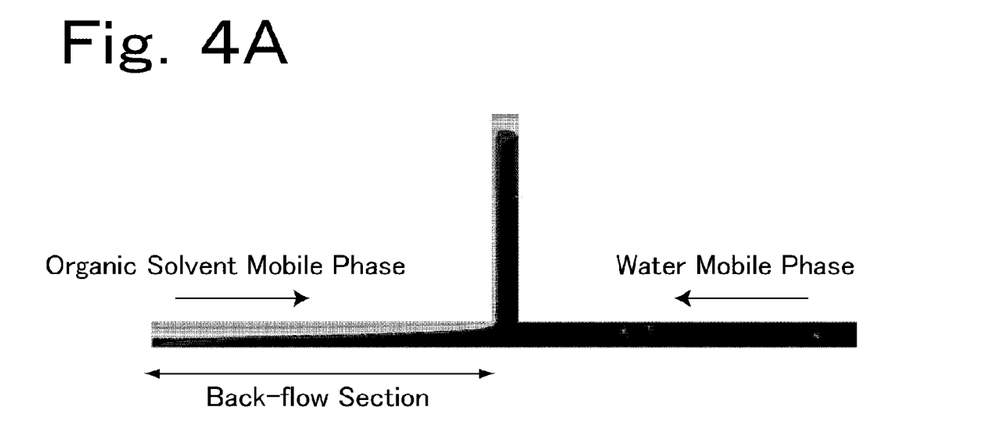
Figure 4B:
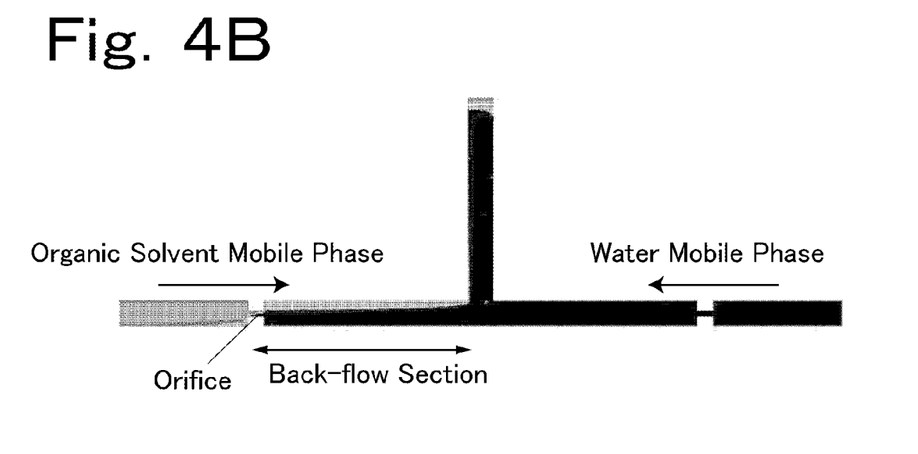

FIGS. 4A and 4B are diagrams showing results of simulations of states in the flow paths in mixing and sending an organic solvent mobile phase and a water mobile phase. FIG. 4A shows a case in which neither of the flow paths is provided with the orifice and FIG. 4B shows a case in which the flow path for sending the organic solvent mobile phase is provided with the orifice.

If the orifice is not provided, when the water mobile phase is suctioned into the reciprocating pump, the water mobile phase having a higher density than the organic solvent mobile phase crawls under the organic solvent mobile phase and flows back into the flow path for the organic solvent mobile phase. On the other hand, if the orifice is provided, the water mobile phase flows back to the orifice in the flow path for the organic solvent mobile phase but hardly flows back to an upstream side of the orifice. Consequently, it is possible to suppress the back-flow of the mobile phase by providing the orifice.

Figure 1:
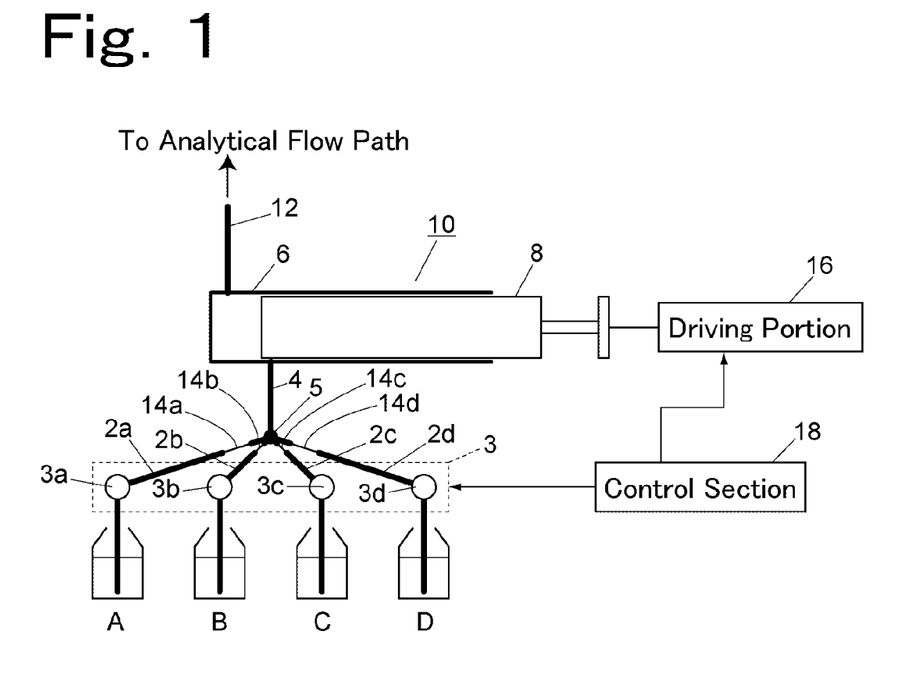
FIG. 1 is a flow path block diagram schematically showing an embodiment of a gradient device.
Figure 2A:
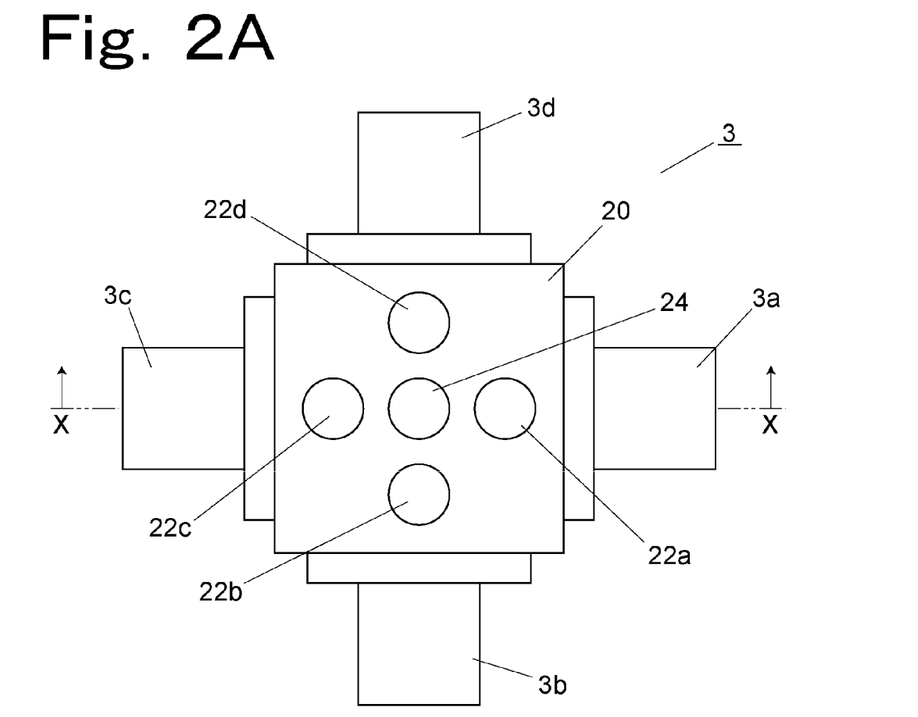
Figure 2B:
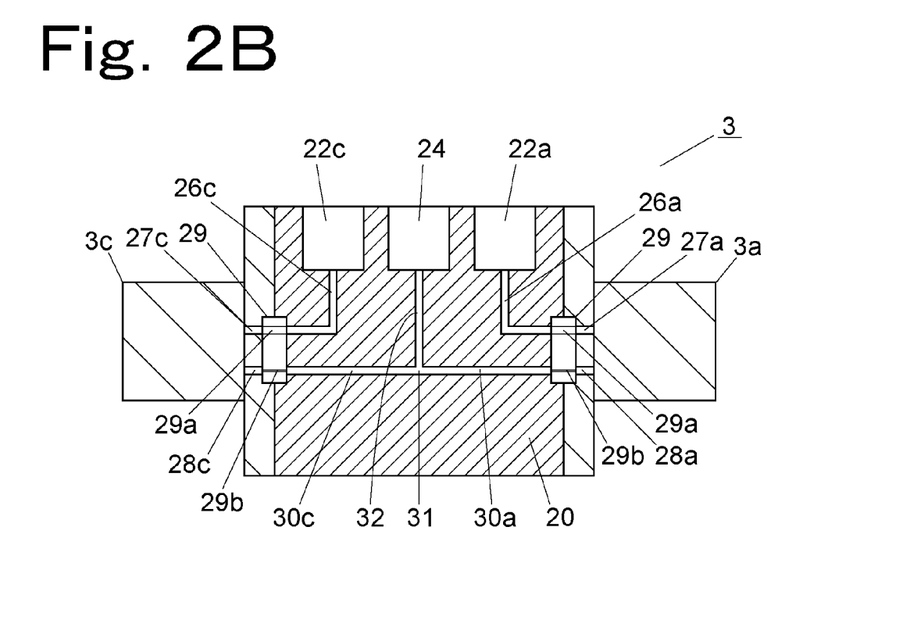
Figure 5A:
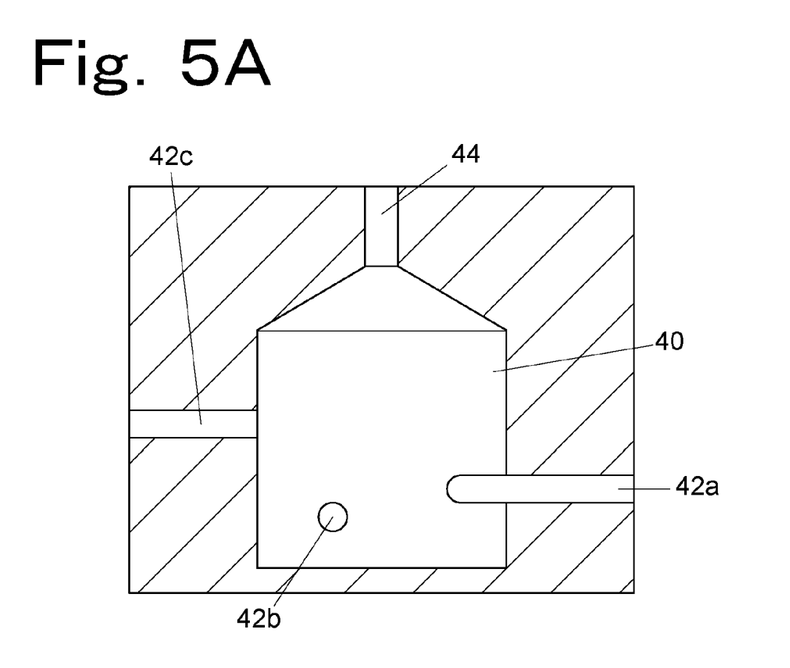
Figure 5B:
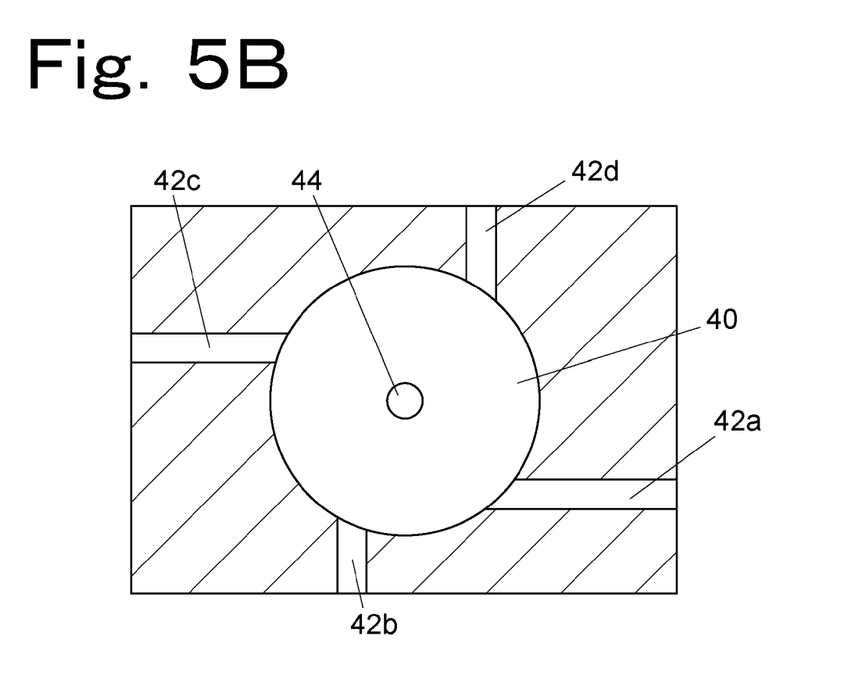

Instead of the structure in FIGS. 2A and 2B, a block in which a plurality of flow paths meet each other may be provided as the meeting portion in FIG. 1. FIGS. 5A and 5B are the conceptual diagrams of a space in the meeting block. As shown in the drawings, by disposing end faces of the flow paths 42a to 42d meeting a meeting space 40 in the meeting block from four directions at such positions that the end faces do not face each other, it is possible to further increase the effect of suppressing the back-flow of the mobile phases.

The invention claimed is:

1. A low-pressure gradient device comprising:
a reciprocating pump for sending a liquid by suctioning and discharging the liquid;
a first suctioning flow path for introducing a first mobile phase into the reciprocating pump;
a second suctioning flow path for introducing a second mobile phase into the reciprocating pump;
a meeting portion where the first suctioning flow path and the second suctioning flow path meet each other;
an inlet flow path connecting the meeting portion and the reciprocating pump;
solenoid valves respectively provided on the first suctioning flow path and the second suctioning flow path to carry out opening and closing of the respective flow paths at different times;
orifices provided as flow path sections having smaller diameters than the other portions of the respective suctioning flow paths between the solenoid valves and the meeting portion on the respective suctioning flow paths; and
a connecting block having the meeting portion and at least a part of each of the suctioning flow paths,
wherein the solenoid valves are attached to the connecting block with respective packings and connected to the respective suctioning flow paths through flow path holes of the respective packings, each of the packing, being sandwiched between the respective solenoid valve and the connecting block, and each of the flow path holes having a constant cross-section, and wherein the orifices are the flow path holes themselves of the respective packings.

2. The low-pressure gradient device according to claim 1, wherein an inner diameter of each of the orifices is half an inner diameter of the respective flow path provided with the respective orifice or smaller.

3. The low-pressure gradient device according to claim 1, wherein end portions of the first suctioning flow path and the second suctioning flow path are disposed at such positions as not to face each other at the meeting portion.

4. The low-pressure gradient device according to claim 1, wherein at least one further suctioning flow path for introducing another mobile phase into the reciprocating pump is connected to the meeting portion, and the further suctioning flow path is also provided with respective solenoid valve and orifice, at least a part of the further suctioning flow path being also formed in the connecting block, the solenoid valve of the further suctioning flow path being also attached to the connecting block with a packing and connected to the further suctioning flow path through a flow path hole of the packing of the further suctioning flow path, the packing being sandwiched between the solenoid valve of the further suctioning flow path and the connecting block and the flow path hole of the packing of the further suctioning flow path having a constant cross-section, and the orifice of the further suctioning flow path being also the flow path hole itself of the packing of the further suctioning flow path.

5. The low-pressure gradient device according to claim 4, wherein an inner diameter of each of the orifices is half an inner diameter of the respective flow path provided with the respective orifice or smaller.

6. The low-pressure gradient device according to claim 4, wherein end portions of the flow paths are disposed at such positions as not to face each other at the meeting portion.

7. The low-pressure gradient device according to claim 4, wherein a fourth suctioning flow path for introducing another mobile phase into the reciprocating pump is connected to the meeting portion, and the fourth suctioning flow path is also provided with respective solenoid valve and orifice.

8. The low-pressure gradient device according to claim 1, wherein the first mobile phase has a higher density than the second mobile phase.

9. The low-pressure gradient device according to claim 1, wherein the first mobile phase is an organic solvent and the second mobile phase is a water solvent.

10. The low-pressure gradient device according to claim 1, wherein the first and the second suctioning flow paths have inner diameters of about 1 to 2 mm and the orifices provided as flow path sections have inner diameter of about 0.3 to 0.6 mm.

* * * * *